United States Patent [19]

Aschwanden et al.

[11] Patent Number: 4,957,911
[45] Date of Patent: Sep. 18, 1990

[54] BENZAZECINE DERIVATIVES FOR COGNITIVE AND MEMORY FUNCTIONS

[75] Inventors: Werner Aschwanden, Ettingen; René Imhof, Gipf-Oberfrick, both of Switzerland; Roland Jakob, Inzlingen, Fed. Rep. of Germany; Emilio Kyburz, Reinach, Switzerland

[73] Assignee: Hoffmann-La Roche Inc., Nutley, N.J.

[21] Appl. No.: 395,380

[22] Filed: Aug. 17, 1989

Related U.S. Application Data

[62] Division of Ser. No. 154,760, Feb. 11, 1988, Pat. No. 4,876,340, which is a division of Ser. No. 121,987, Nov. 18, 1987, Pat. No. 4,749,791, which is a division of Ser. No. 5,712, Jan. 21, 1987, Pat. No. 4,732,979.

[30] Foreign Application Priority Data

Jan. 23, 1986 [CH] Switzerland ............................ 266/86

[51] Int. Cl.$^5$ .................. A61K 31/395; C07P 227/08
[52] U.S. Cl. ..................... 514/183; 540/461; 540/463
[58] Field of Search ................. 540/461, 463; 514/183

[56] References Cited

U.S. PATENT DOCUMENTS

| | | | |
|---|---|---|---|
| 2,313,138 | 3/1943 | Frohlich et al. | 546/101 |
| 4,341,786 | 7/1982 | de Marinis et al. | 546/101 |
| 4,521,423 | 6/1985 | Asselin et al. | 546/101 |
| 4,732,979 | 3/1988 | Aschwanden et al. | 540/461 |
| 4,749,791 | 6/1988 | Aschwanden et al. | 540/461 |
| 4,876,340 | 10/1989 | Aschwanden et al. | 540/461 |

FOREIGN PATENT DOCUMENTS 4945874 12/1974 Japan ........................... 540/461

Primary Examiner—Glennon H. Hollrah
Assistant Examiner—Mark W. Russell
Attorney, Agent, or Firm—George M. Gould; Bernard S. Leon; Alan P. Kass

[57] ABSTRACT

Benzazecinediones of the formula

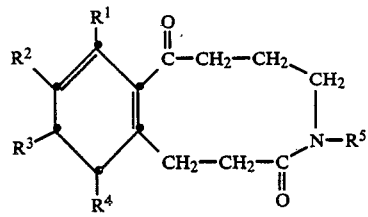

wherein $R^1$ and $R^2$ are independently hydrogen or chlorine, $R^3$ is hydrogen, fluorine, chlorine, bromine or methoxy, $R^4$ is hydrogen, chlorine or methoxy and $R^5$ is hydrogen, acetyl, propionyl, benzoyl, chlorobenzoyl, methoxybenzoyl or phenylacetyl, with the proviso that 2 or 3 of the groups $R^1$ to $R^4$ are hydrogen, as well as many of the corresponding benzo[f]quinolines from which these benzazecinediones can be prepared by oxidation are suitable for the control or prevention of cerebral insufficiency or for the improvement of cognitive functions in mammals. They can be produced according to various processes and can be prepared into pharmaceutical compositions.

4 Claims, No Drawings

BENZAZECINE DERIVATIVES FOR COGNITIVE AND MEMORY FUNCTIONS

This is a division, of application Ser. No. 07/154,760, now U.S. Pat. No. 4,876,340 field Feb. 11, 1988, which is a division of application Ser. No. 07/121,987, now U.S. Pat. No. 4,749,791 filed Nov. 18, 1987, which is a divisional of 07/005,7112 now U.S. Pat. 4,732,979 filed Jan. 21, 1987.

BACKGROUND OF THE INVENTION

The present invention is concerned with benzazecine derivatives. In particular, it is concerned with compounds of the formula

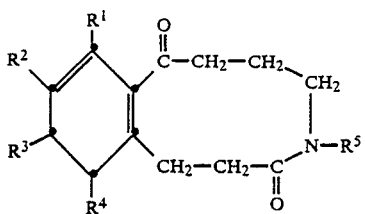

wherein $R^1$ and $R^2$ each is independently hydrogen or chlorine, $R^3$ is hydrogen, fluorine, chlorine, bromine or methoxy, $R^4$ is hydrogen, chlorine or methoxy and $R^5$ is hydrogen, acetyl, propionyl, benzoyl, chlorobenzoyl, methoxybenzoyl or phenylacetyl, with the proviso that 2 or 3 of the groups $R^1$ to $R^4$ are hydrogen.

These compounds are characterized by valuable pharmacodynamic properties.

DESCRIPTION OF THE INVENTION

The present invention includes the compounds of formula I, a process and intermediates for the preparation of such compounds, pharmaceutical compositions containing such compounds and a process for the preparation of such pharmaceutical compositions, and also the use of the compounds of formula I or of the pharmaceutical compositions in the control or prevention of illnesses or in the improvement of health, especially in the control or prevention of cerebral insufficiency or in the improvement of cognitive functions. The compounds of formula I are particularly useful in the enhancement of memory retention and in the improvement of learning capability.

The term "lower" used in the present description denotes residues or compounds which contain a maximum of 7, preferably a maximum of 4, carbon atoms. The term "alkyl" denotes straight-chain or branched saturated hydrocarbon residues such as methyl, ethyl, n-propyl, isopropyl, n-butyl, isobutyl, s-butyl, t-butyl and the like. The term "acyl" denotes residues which are derived from organic acids by elimination of the hydroxyl group and, accordingly, embraces, for example, alkanoyl residues (such as acetyl, propionyl, and the like), aroyl residues (such as benzoyl, p-chlorobenzoyl, o-methoxybenzoyl. m-methoxybenzoyl, p-methoxybenzoyl, and the like). aryl-alkanoyl residues (such as phenylacetyl, and the like), and so forth.

Among the compounds of formula I there are preferred those in which $R^1$ is chlorine and $R^2$, $R^3$ and $R_4$ each is hydrogen, or $R^2$ is chlorine and $R^1$, $R^3$ and $R^4$ is hydrogen, or $R^3$ is fluorine, chlorine, bromine or methoxy and $R^1$, $R^2$ and $R^4$ are hydrogen, or $R^4$ is chlorine or methoxy and $R^1$, $R^2$ and $R^3$ each is hydrogen, or $R^1$ and $R^3$ each is chlorine and $R^2$ and $R^4$ each is hydrogen. The preferred meaning of and the symbol $R^5$ in formula I is acetyl.

Especially preferred compounds of formula I are the following:
4-Acetyl-9-chloro-1,2,4,5,6,7-hexahydro-4-benzazecine-3,8-dione,
4-acetyl-11-chloro-1,2,4,5,6,7-hexahydro-4-benzazecine-3,8-dione,
4-acetyl-11-fluoro-1,2,4,5,5,6,7-hexahydro-4-benzazecine-3,8-dione and
4-acetyl-9,11-dichloro-1,2,4,5,6,7-hexahydro-4-benzazecine-3,8-dione.

Further preferred compounds of formula I are:
4-Acetyl-11-methoxy-1,2,4,5,6,7-hexahydro-4-benzazecine-3,8-dione,
11-chloro-1,2,4,5,6,7-hexahydro-4-propionyl-4-benzazecine-3,8-dione,
4-benzoyl-11-chloro-1,2,4,5,6,7-hexahydro-4-benzazecine-3,8-dione,
4-(o-methoxybenzoyl)-11-chloro-1,2,4,5,6,7-hexahydro-4-benzazecine-3,8-dione,
4-(m-methoxybenzoyl)-11-chloro-1,2,4,5,6,7-hexahydro-4-benzazecine-3,8-dione,
4-(p-methoxybenzoyl)-11-chloro-1,2,4,5,6,7-hexahydro-4-benzazecine-3,8-dione,
11-chloro-4-(p-chlorobenzoyl)-1,2,4,5,6,7-hexahydro-4-benzazecine-3,8-dione and
4-acetyl-1,2,4,5,6,7-hexahydro-12-methoxy-4-benzazecine- -3,8-dione.

Representative examples of compounds of formula I are also:
9-Chloro-1,2,4,5,6,7-hexahydro-4-benzazecine-3,8-dione;
4-acetyl-10-chloro-1,2,4,5,6,7, -hexahydro-4-benzazecine-3,8-dione;
11-chloro-1,2,4,5,6,7-hexahydro-4-(phenylacetyl)-4-benzazecine-3,8-dione;
11-chloro-1,2,4,5,6,7-hexahydro-4-benzazecine-3,8-dione;
4-acetyl-11-bromo-1,2,4,5,6,7-hexahydro-4-benzazecine-3.8-dione; and
4-acetyl-12-chloro-1,2,4,5,6,7-hexahydro 4-benzazecine-3,8-dione.

The compounds of formula I can be prepared in accordance with the invention by (a) oxidizing a benzoquinoline derivative having the formula

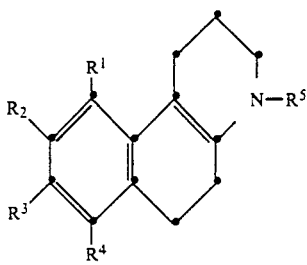

wherein $R^1$, $R^2$, $R^3$, $R^4$ and $R^5$ are defined the same as above, or (b) removing the group denoted by Z from a benzazecine derivative having the formula

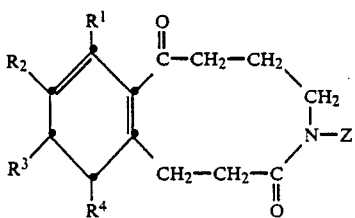

III wherein $R^1$, $R^2$, $R^3$ and $R^4$ are defined as above and Z is a cleavable group.

The compounds of formula II, above, are also an aspect of the present invention, as is a process for their preparation, which comprises (a) reducing a benzoquinolinone derivative having the formula

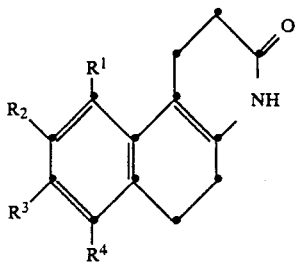

IV wherein $R^1$, $R^2$, $R^3$ and $R^4$ are defined as above, or (b) reacting a compound of the formula

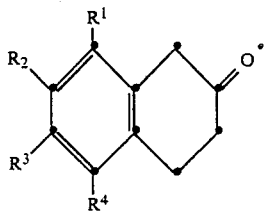

V wherein $R^1$, $R^2$, $R^3$ and $R^4$ are defined as above, in the presence of a strong base with a compound of the formula

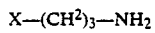

X—(CH$^2$)$_3$—NH$_2$   VI wherein X is a leaving group, and, if desired, N-substituting the obtained compound of formula II, in which $R^5$ is hydrogen, with acetyl, propionyl, benzoyl, chlorobenzoyl, methoxybenzoyl or phenylacetyl.

Many of the compounds of formula II have pharmacodynamic properties similar to those of the formula I compounds, especially the following:
4-acetyl-8-chloro-1,2,3,4,5,6-hexahydrobenzo[f]-quinoline,
4-acetyl-10-chloro-1,2,3,4,5,6-hexahydrobenzo[f]-quinoline and
8-chloro-4-(p-chlorobenzoyl)-1,2,3,4,5,6-hexahydrobenzo[f]quinoline.

The present invention also encompasses pharmacodynamically active compounds of formula II as pharmaceutical active substances, pharmaceutical compositions containing compounds of formula II and processes for the preparation of such compositions, as well as the use of such compounds and compositions in the control or prevention of illnesses or in the improvement of health, especially in the control or prevention of cerebral insufficiency or in the improvement of cognitive functions, as already described for the compounds of formula I.

Those compounds of formula III in which Z is acetyl, propionyl, benzoyl, chlorobenzoyl, methoxybenzoyl or phenylacetyl fall under the scope of formula I. Those compounds of formula III in which Z is another cleavable group are also within the scope of the present invention.

The oxidation in accordance with the invention of benzoquinoline derivatives having formula II to corresponding benzazecine derivatives having formula I is conveniently effected by means of m-chloroperbenzoic acid in an inert organic solvent, for example, in a halogenated hydrocarbon such as chloroform and the like. The temperature is not critical, and the oxidation can be effected conveniently at temperatures of about −20° C. to about 30° C., preferably between about −5° C. and about room temperature.

Furthermore, this oxidation can also be carried out conveniently by means of potassium permanganate and sodium periodate, conveniently in a two-phase system consisting of water and an organic solvent which is not miscible therewith, for example, a halogenated hydrocarbon such as methylene chloride and the like. In this case, there is preferably added a phase transfer catalyst, especially a quaternary ammonium salt such as benzyltriethylammonium chloride or the like. Again, the reaction temperature is not critical and the oxidation by means of potassium permanganate/sodium periodate can be carried out conveniently at temperatures between about 0° C. and about 30° C., preferably at about room temperature.

Moreover, oxidation agents or oxidation systems such as peracetic acid, hydrogen peroxide and formic acid or p-toluenesulphonic acid, chromosulphuric acid, Jones reagent, and the like, are suitable for carrying out this oxidation in reaction.

When $R^5$ in formula II is hydrogen, then the oxidation to the corresponding compounds of formula I proceeds very readily, under certain circumstances even spontaneously by the influence of the oxygen present in the atmosphere.

Compounds of formula I can also be obtained in accordance with this invention by removing the cleavable group Z from a compound of formula III. As cleavable groups there are suitable readily cleavable acyl groups such as acetyl and the like.

The cleavage of an acetyl group is conveniently effected under alkaline conditions, for example, by means of potassium carbonate, sodium hydrogen carbonate, and the like, in a mixture of water and an organic solvent which is miscible therewith (for example, a lower alkanol such as methanol), or by means of an alkali metal lower alkoxide in a organic solvent which is inert under the reaction conditions, conveniently in the corresponding lower alkanol, etc.

The reduction in accordance with the invention of a compound of formula IV to the corresponding benzoquinoline derivative of formula II in which $R^5$ is hydrogen is conveniently effected by means of a complex hydride such as lithium aluminum hydride, or the like, in an organic solvent which is inert under the reduction conditions, conveniently in an ether such as tetrahydrofuran, dioxan, and the like. The reaction temperature is not critical, and the reduction can be effected at temperatures between about room temperature and about 120° C., preferably at the reflux temperature.

The reaction in accordance with the invention of a compound of formula V with a compound of formula VI is effected in the presence of a strong base, conveniently in the presence of an inorganic base such as potassium or sodium hydroxide, or a quaternary ammonium base such as benzyltrimethylammonium hydroxide. The leaving group denoted by the symbol X in formula VI is preferably a halogen atom, especially a chlorine atom, but other equivalent leaving groups are also possible, for example. alkylsulphonyloxy groups such as mesyloxy, or arylsulphonyloxy groups such as benzenesulphonyloxy, p-toluenesulphonyloxy, p-bromobenzenesulphonyloxy and the like. The compound of formula VI is conveniently used in the form of an acid addition salt, for example, as the hydrochloride. The reaction is effected in the presence of an organic solvent which is inert under the reaction conditions, for example, in a lower alkanol such as methanol, an aromatic hydrocarbon such as toluene, and the like.

The reaction temperature is not critical, and the reaction of the compounds of formula V and VI can be effected conveniently at between temperatures of about 30° C. and about 110° C., preferably at the reflux temperature.

Not only in the reduction of a compound of formula IV, but also in the reaction of compounds of formulae V and VI there are obtained corresponding compounds of formula II in which $R^5$ is hydrogen. These can be appropriately N-acylated in accordance with the invention, conveniently in situ, that is, without isolating them. As acylating agents there are used in this case the reactive derivatives of the corresponding carboxylic acids which yield the desired acyl residue, conveniently anhydrides such as acetic anhydride, propionic anhydride and the like, carboxylic acid chlorides such as benzoyl chloride, p-chlorobenzoyl chloride, o-methoxybenzoyl chloride, m-methoxybenzoyl chloride, p-methoxybenzoyl chloride, phenylacetyl chloride etc, and the like. In an analogous manner there are obtained compounds of formula III which do not fall under the scope of formula I, that is, in which Z is different from acetyl, propionyl, benzoyl, chlorobenzoyl, methoxybenzoyl or phenylacetyl, namely by treating corresponding compounds of formula II in which $R^5$ is hydrogen with an agent which yields the desired group Z, for example, by means of benzyloxycarbonyl chloride or the like.

The preparation of compounds of formulae IV and V is conveniently effected in accordance with the following Reaction Scheme, in which $R^1$, $R^2$, $R^3$ and $R^4$ have the above-mentioned meanings and $R^6$ and $R^7$ each is lower alkyl or together with the nitrogen atom a heterocyclic residue such as pyrrolin-1-yl, pyrrolidin-1-yl, piperidino, morpholino, 4-(lower alkyl)-piperazin-1-yl, and the like.

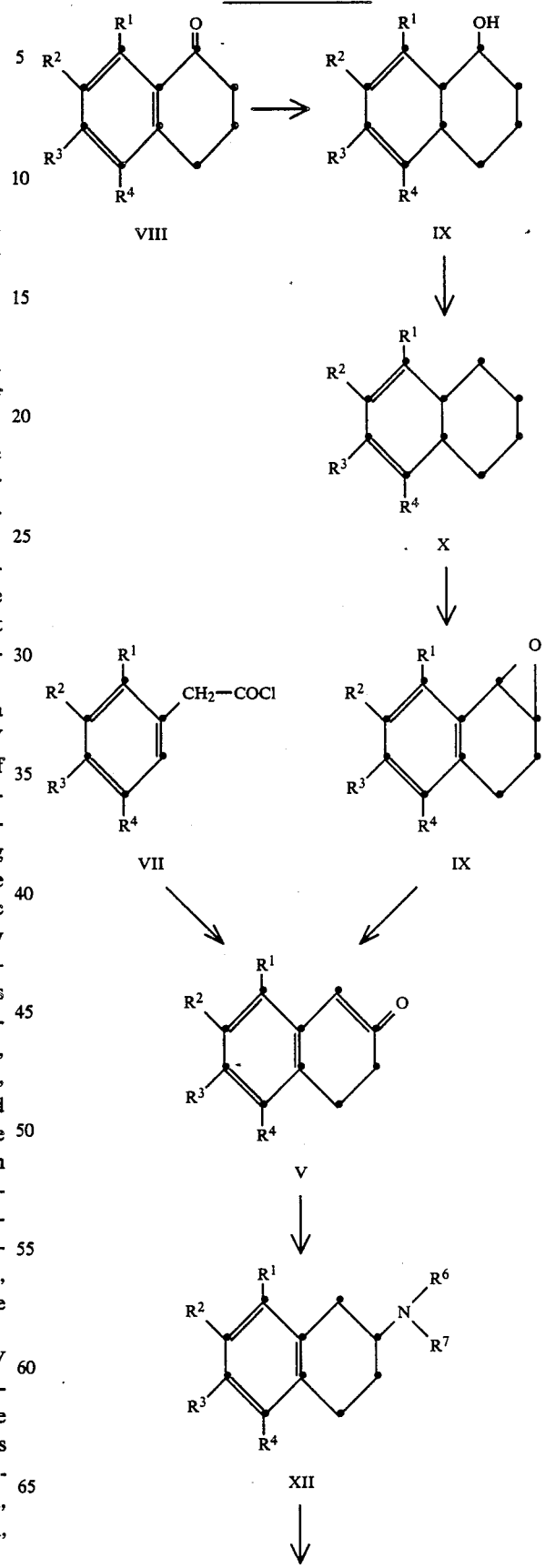

-continued
Reaction Scheme

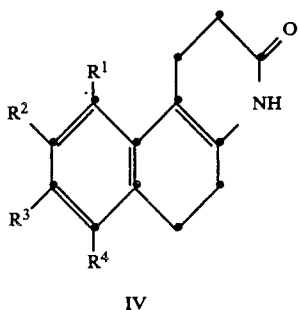

IV

Compounds of formula V can be prepared in one step from compounds of formula VII by reaction with ethylene in the presence of aluminum chloride or another Lewis acid which is suitable as a catalyst for such reactions. The reaction is effected in the presence of an organic solvent which is inert under the reaction conditions, conveniently in a halogenated hydrocarbon such as methylene chloride.

Compounds of formula V can, however, also be prepared by a multi-step synthesis starting from compounds of formula VIII. First, the compound of formula VIII is reduced to the corresponding compound of formula IX, conveniently with a complex hydride such as sodium borohydride or the like. The compound of formula IX is then dehydrated to the corresponding compound of formula X, conveniently under acidic conditions, for example, by means of a strong acid such as p-toluenesulphonic acid or the like in a solvent which is not miscible with water but which distils azeotropically at reflux temperature, in which the water which results is removed continuously. The compound of formula X is then oxidized to the corresponding compound of formula XI. This oxidation is conveniently effected by means of m-chloroperbenzoic acid or the like in an organic solvent which is inert under the reaction conditions, for example, in a chlorinated hydrocarbon such as methylene chloride. Compounds of formula V are then obtained from corresponding compounds of formula XI, for example, by treatment with an ethereal solution of magnesium bromide or by treatment with an organic sulphonic acid such as p-toluenesulphonic acid or the like in an inert organic solvent such as toluene or the like.

For the preparation of a compound of formula XII, a corresponding compound of formula V is reacted with a secondary amine of the formula $HNR^6R^7$, such as for example, pyrrolidine, in the presence of an acid, conveniently an organic sulphonic acid such as p-toluenesulphonic acid or the like, in an organic solvent which is inert under the reaction conditions, for example, in an aromatic hydrocarbon such as benzene. The water which thereby results is removed from the reaction system, for example, by the addition of molecular sieve or by azeotropic distillation. Compounds of formula IV are finally obtained by reacting a corresponding compound of formula XII with acrylamide, conveniently in the presence of an acid, for example, an organic sulphonic acid such as p-toluenesulphonic acid, or an acidic ion exchanger, or the like, at temperatures of about 100° C. to about 200° C., preferably of about 100°-150° C., whereby lower alkanols, such as ethanol or the like, can be used as the solvent.

As mentioned above, the compounds of formula I are compounds with valuable pharmacodynamic properties, and the same also applies to many of the compounds of formula II. Both the compounds of formula I and the pharmaceutically active compounds of formula II are useful to control cerebral insufficiencies and to improve learning in mammals. They have a low toxicity, and it has been shown that in the animal experiment described below, they are capable of counteracting experimentally induced cerebral insufficiency.

IN VIVO TEST PROCEDURE (RATS)

The test apparatus is a "Skinner box" with an electrifiable grid floor (30×40 cm) and a grey plastic platform (15×15×0.8 cm) in the front right corner. Untrained male rats (100–120 g) are placed individually on the platform. As soon as they climb down on to the grid floor they receive a mild electric foot-shock (0.8 mA). The normal reaction of untrained rats is to climb back on to the platform. The foot-shock procedure must be repeated three to five times for each animal, after which the rats have acquired a "passive avoidance response", that is, they no longer attempt to descend from the platform to the grid floor.

Immediately thereafter three groups, each comprising 30 animals, are set up. The first group receives an injection (i.p.) of 0.3 mg/kg of scopolamine as well as distilled water (2 ml/kg p.o.). The second group receives an injection (i.p.) of 0.3 mg/kg of scopolamine and an oral dosage of the test substance. The third group receives only distilled water (p.o.).

Two hours later, each rat is placed once on the platform in the "Skinner box". The criterion for the assessment of the effect of a test compound or preparation on the short-time memory is whether the animal remains or does not remain for 60 seconds on the platform (the result can thus only read "yes" or "no" for each animal). The statistical significance of the difference between the results obtained in the first and in the second groups is determined by means of the Chi-Square test.

70–75% of the animals treated only with distilled water (p.o.) still remember 2–4 hours after learning the "passive avoidance response" that they should remain on the platform. In the case of 85–92% of the animals treated with scopolamine (0.3 mg/kg i.p.) and distilled water (p.o.). there is demonstrated during 3–4 hours a retrograde effect on the short-time memory, that is, they have forgotten that they must remain on the platform. A substance which is capable of counteracting cerebral insufficiency can reverse the blocking of the short-time memory caused by the injection (i.p.) of 0.3 mg/kg of scopolamine. A dosage of a preparation is denoted as "active" against scopolamine if the number of positive results ("yes") is significantly different from those of control animals treated with scopolamine (0.3 mg/kg i.p.) and only distilled wayer (p.o.).

In the following Table there are given dosages in which certain compounds of formulae I and II exhibit a significant activity in the test previously described. Moreover, the Table contains data for the acute toxicity ($LD_{50}$ in mg/kg in the case of single oral administration to mice).

TABLE

| Formula | $R^1$ | $R^2$ | $R^3$ | $R^4$ | $R^5$ | Significant active dosage mg/kg p.o. | LD 50 mg/kg p.o. |
|---|---|---|---|---|---|---|---|
| I | Cl | H | H | H | $COCH_3$ | 0.1 | >5000 |

TABLE-continued

| Formula | R¹ | R² | R³ | R⁴ | R⁵ | Significant active dosage mg/kg p.o. | LD 50 mg/kg p.o. |
|---|---|---|---|---|---|---|---|
| | | | | | | 0.3 | |
| | | | | | | 1 | |
| | | | | | | 3 | |
| | | | | | | 10 | |
| | | | | | | 30 | |
| I | H | H | Cl | H | COCH₃ | 0.001 | >5000 |
| | | | | | | 0.003 | |
| | | | | | | 0.01 | |
| | | | | | | 0.03 | |
| I | H | H | F | H | COCH₃ | 0.03 | >5000 |
| | | | | | | 0.1 | |
| | | | | | | 0.3 | |
| | | | | | | 1 | |
| | | | | | | 3 | |
| | | | | | | 10 | |
| I | Cl | H | Cl | H | COCH₃ | 0.03 | >5000 |
| | | | | | | 0.1 | |
| | | | | | | 0.3 | |
| | | | | | | 1 | |
| II | H | H | Cl | H | COCH₃ | 0.01 | 2500–5000 |
| | | | | | | 0.03 | |
| | | | | | | 0.1 | |
| | | | | | | 0.3 | |
| II | Cl | H | H | H | COCH₃ | 0.3 | |
| | | | | | | 1 | |
| | | | | | | 3 | |
| | | | | | | 10 | |

The compounds of formula I and pharmacodynamically active compounds of formula II can be used as therapeutic ingredients, for example, in the form of pharmaceutical compositions. The pharmaceutical compositions can be administered orally, as in the form of tablets, coated tablets, dragees, hard and soft gelatine capsules, solutions, emulsions or suspensions. The administration can, however, also be effected rectally, for example, in the form of suppositories, or parenterally, for example, in the form of injection solutions.

As mentioned earlier, pharmaceutical compositions containing a compound of formula I and/or a pharmacodynamically active compound of formula II are also a facet of the present invention, as is a process for the preparation of such pharmaceutical compositions which comprises bringing one or more compounds of formula I and/or pharmacodynamically active compounds of formula I and, if desired, one or more other therapeutically active substances into a galenical administration form together with one or more therapeutically inert excipients.

For the preparation of tablets, coated tablets, dragees and hard gelatine capsules there can be used as excipients materials such as lactose, maize starch or derivatives thereof, talc, stearic acid or its salts, and so forth.

For soft gelatine capsules there are suitable as excipients materials such as vegetable oils, waxes, fats, semi-solid and liquid polyols, and so forth.

For the manufacture of solutions and syrups there are suitable as excipients materials such as water, polyols, saccharose, invert sugar, glucose, and the like.

For injection solutions there are suitable as excipients materials such as water, alcohols, polyols, glycerine, vegetable oils, and so forth.

For suppositories there are suitable as excipients materials such as natural or hardened oils, waxes, fats, semi-liquid or liquid polyols and the like.

The pharmaceutical preparations can contain, in addition, preserving agents, solubilizers, stabilizing agents, wetting agents, emulsifying agents, sweetening agents, coloring agents, flavoring agents, salts for varying the osmotic pressure, buffers, coating agents or antioxidants. They can also contain other therapeutically useful substances.

In accordance with the present invention, the compounds of formula I and/or pharmacodynamically active, compounds of formula II can be used in the control or prevention of cerebral insufficiency or in the improvement of cognitive functions (such as memory retention, learning capability, interest in the surroundings and self-care), for example in geriatry, in the case of intoxications such as alcoholism and in the case of cerebro-vascular disorders. Further possible fields of use are vestibular disorders (such as Meniere's disease) and development disorders (such as dyslexia). The dosage can vary within wide limits and will, of course, be fitted to the individual requirements in each particular case. In general, in the case of oral administration a daily dosage of about 10 to 2500 mg should be appropriate, however, the upper limit just given can be exceeded when this is shown to be indicated.

Finally, the use of the compounds of formula I and/or of pharmacodynamically active compounds of formula II for the preparation of pharmaceutical compositions for the control or prevention of cerebral insufficiency or for the improvement of cognitive functions is also an object of the invention.

In the following Examples, which illustrate the present invention, but are not intended to be limiting, all temperatures are given in degrees Celsius.

EXAMPLE 1

(a) 154.8 g of 2-chlorophenylacetyl chloride dissolved in 290 ml of methylene chloride were added dropwise within 1 hour to 218 g of aluminum chloride in 1000 ml of methylene chloride while stirring at between 0° and 5°. Thereafter, ethylene was introduced into the mixture at between 0° and 5° during 40 minutes, whereupon the reaction mixture was stirred at room temperature for 1 hour and then treated at between 0° and 5° with 570 ml of cold water. The methylene chloride phase was washed with 2×500 ml of 2N hydrochloric acid, 2×500 ml of sodium hydrogen carbonate solution and 700 ml of water. The aqueous phases were extracted with 300 ml of methylene chloride. The combined methylene chloride phases were dried over sodium sulphate and concentrated in vacuo. The 8-chloro-3,4-dihydro-2(1H)-naphthalenone, crystallized from 400 ml of low-boiling petroleum ether, exhibits a melting point of 56°–59°.

(b) 70.0 g of 8-chloro-3,4-dihydro-2(1H)-naphthalenone were boiled at reflux for 2.5 hours in 550 ml of benzene and 33 ml of pyrrolidine in the presence of 1.4 g of p-toluenesulphonic acid. The crude 1-(8-chloro-3,4-dihydro-2-naphthyl)-pyrrolidine obtained was processed without purification.

(c) 56.0 g of acrylamide and 3.0 g of anhydrous p-toluenesulphonic acid were added to 89.4 g of crude 1-(8-chloro-3,4-dihydro-2-naphthyl) pyrrolidine. The mixture was heated under nitrogen to 100° for 2 hours and to 150° for 2 hours. The reaction mixture was partitioned between 300 ml of methylene chloride and 200 ml of water. The organic phase was washed with water and filtered through 500 g of silica gel (particle size 0.2–0.5 mm). The 10-chloro-1,4,5,6-tetrahydrobenzo[h]quinolin-3(2H)-one, eluted with ethyl acetate, exhibits a melting point of 186°–187° after recrystallization from ethyl acetate.

(d) 20.0 g of 10-chloro-1,4,5,6-tetrahydrobenzo[h]-quinolin-3(2H)-one were added portionwise within 35 minutes at between 20° and 25° to a suspension, stirred under nitrogen, of 6.49 g of lithium aluminum hydride in 240 ml of dry tetrahydrofuran. The reaction mixture was subsequently heated to boiling under reflux for 150 minutes, then cooled and thereupon treated at between 0° and 10° with 21.0 ml of 6.5 N sodium hydroxide solution. The resulting suspension was filtered, whereupon the filter residue was rinsed several times with 20 ml of tetrahydrofuran each time and the filtrate was evaporated in vacuo. The thus-obtained 10-chloro-1,2,3,4,5,6-hexahydrobenzo[f]-quinoline was processed directly.

(e) 20.1 g of crude .1-chloro-1,2,3,4,5,6-hexahydrobenzo-[f]quinoline were taken up in 40 ml of pyidine and 36 ml of acetic anhydride. The reaction mixture was left to stand at room temperature for 20 hours, evaporated, the residue remaining behind was taken up twice in 150 ml of dry toluene each time and the solutions obtained were evaporated to dryness. The residue was dissolved in methylene chloride and chromatographed on 150 g of silica gel (particle size 0.2–0.5 mm). The 4-acetyl-10-chloro-1,2,3,4,5,6-hexahydrobenzo[f-]quinoline, eluted with chloroform, exhibits a melting point of 117°–118° after recrystallization from isopropyl ether.

(f) 8.5 g of 4-acetyl-10-chloro-1,2,3,4,5,6-hexahydrobenzo[f]quinoline were dissolved in 205 ml of chloroform, whereupon 16 g of 85% m-chloroperbenzoic acid dissolved in 205 ml of chloroform were added dropwise at 0° to +5°. After stirring at room temperature for 4 hours 4 g of potassium iodide and 70 ml of water were added to the reaction mixture, whereupon it was treated with sodium thiosulphate until decolorization occured. The chloroform phase was washed with 70 ml of 2N sodium hydroxide solution and 2×170 ml of water. The aqueous phases were extracted with 170 ml of chloroform. The combined chloroform extracts were dried and evaporated in vacuo. The residue was dissolved in methylene chloride and chromatographed on 100 g of silica gel (particle size 0.2–0.5 mm). The 4-acetyl-9-chloro-1,2,4,5,6,7-hexahydro-4-benzazecine-3,8-dione, eluted With methylene chloride, exhibits a melting point of 115°–116° after recrystallization from isopropyl ether.

EXAMPLE 2

7.60 g of 4-acetyl-9-chloro-1,2,4,5,6,7-hexahydro-4-benzazecine-3,8-dione were dissolved in 240 ml of methanol and treated with a mixture of 36 ml of methanol and 4 ml of saturated potassium carbonate solution. The mixture was stirred at room temperature for 1 hour and thereafter the solvent was removed in vacuo. The residue was triturated in ethyl acetate. The crystallized-out 9-chloro-1,2,4,5,6,7-hexahydro-4-benzazecine-3,8-dione was filtered off and exhibited a melting point of 211°–214°. The filtrate was chromatographed on 100 g of silica gel (particle size 0.2–0.5 mm). A further portion of 9-chloro-1,2,4,5,6,7-hexahydro-4-benzazecine-3.8-dione can be isolated from the ethyl acetate eluate.

EXAMPLE 3

5.0 g of 8-chloro-3,4-dihydro-2(1H)-naphthalenone, 115 ml of benzene and 17 ml of Triton-B (40% in methanol) were boiled at reflux, whereupon 5.0 g of 3-chloropropylamine hydrochloride dissolved in 25 ml of methanol were added dropwise and the mixture was heated at reflux for a further 5 hours. 5 g of molecular sieve 4A were then added, whereupon the mixture was boiled at reflux for a further 20 hours. After filtration the reaction mixture was concentrated in a water-jet vacuum, whereupon the residue was partitioned between diethyl ether and 3N hydrochloric acid and the organic phase was extracted a further twice with 3N hydrochloric acid. The hydrochloric acid phases were made basic with 2N sodium hydroxide solution and extracted with ethyl acetate. The ethyl acetate phases were washed with sodium chloride solution, dried and evaporated in vacuo. The residue was chromatographed through 300 g of silica gel (particle size 0.2–0.5 mm). The 9-chloro-1,2,4,5,6,7-hexahydro-4-benzazecine-3,8-dione, eluted with methylene chloride-ethyl acetate (mixture 1:1) and ethyl acetate, exhibits a melting point of 196°–198° after trituration in diethyl ether. After recrystallization from ethyl acetate the product exhibits a melting Point of 207°–208°.

In the above Example there was first formed 10-chloro-1,4,5,6-tetrahydrobenzo[h]quinolin-3(2H)-one which was not isolated but converted by air oxidation into 9-chloro-1,2,4,5,6,7-hexahydro-4-benzazecine-3,8-dione.

EXAMPLE 4

(a) 11.0 g of 7-chloro-3,4-dihydro-2(1H)-naphthalenone was boiled at reflux for 2 hours in 200 ml of benzene and 6.0 ml of pyrrolidine in the presence of 0.25 g of p-toluenesulphonic acid. The 1-(7-chloro-3,4-dihydro-2-naphthyl)pyrrolidine obtained was recrystallized from 150 ml of isopropyl ether and exhibits a melting point of 115°–116°.

(b) 6.45 g of acrylamide were added to 10.6 g of 1-(7-chloro-3,4-dihydro-2-naphthyl)pyrrolidine. The mixture was heated under nitrogen to 100° for 2 hours and to 150° for 2 hours. The reaction mixture was treated with 100 ml of ethyl acetate, whereupon the resulting mixture was stirred at room temperature and there was filtered off the 9-chloro-1,4,5,6-tetrahydrobenzo[f]quinolin-3(2H)-one which melts at 265°–267° after recrystallization from ethyl acetate.

(c) 4.9 g of 9-chloro-1,4,5,6-tetrahydrobenzo[f]quinolin-3(2H)-one were added portionwise over a period of 35 minutes at between 20° and 25° to a suspenion, stirred at 20° under nitrogen, of 1.59 g of lithium aluminium hydride in 60 ml of dry tetrahydrofuran. The reaction mixture was subsequently boiled at reflux for 150 minutes, then cooled and thereupon treated at between 0° and 10° with 5.20 ml of 6.5N sodium hydroxide solution. The resulting suspension was filtered, whereupon the filter residue was rinsed several times with 20 ml of tetrahydrofuran each time and the filtrate was evaporated in vacuo. The thus-obtained 9-chloro-benzo[f-]quinoline was taken up as the crude product in 10 ml of pyridine and 9.0 ml of acetic anhydride. The reaction mixture was left to stand at room temperature for 20 hours, then evaporated, the residue remaining behind was taken up twice in 50 ml of dry toluene each time and the solutions obtained were evaporated to dryness. The residue was dissolved in methylene chloride and chromatographed on 150 g of silica gel (particle size 0.2–0.5 mm). The 4-acetyl-9-chlorobenzo [f]quinoline, eluted with methylene chloride, exhibits a melting point of 151.5°–152° after recrystallization from isopropyl ether.

(d) 2.5 g of 4-acetyl-9-chlorobenzo[f]quinoline were dissolved in 60 ml of chloroform, whereupon 5.02 g of 85% m-chloroperbenzoic acid dissolved in 60 ml of chloroform were added dropwise at 0° to +5°. The mixture was thereafter stirred at room temperature for 3 hours. 0.4 g of potassium iodide and 40 ml of water were added to the reaction mixture, whereupon the resulting mixture was treated with sodium thiosulphate until decolorization occured. The chloroform phase was separated and washed with 40 ml of 2N sodium hydroxide solution and then with 2×50 ml of water. The aqueous phases were extracted with 100 ml of chloroform. The combined chloroform extracts were dried and evaporated in vacuo. The 4-acetyl-10-chloro-1,2,4,5,6,7-hexahydro-4-benzazecine-3,8-dione, recrystallized from isopropyl ether, exhibits a melting point of 136°-137°.

EXAMPLE 5

(a) 149.4 g of 4-fluorophenylacetyl chloride dissolved in 300 ml of methylene chloride were added dropwise within 60 minutes to 230 g of aluminum chloride in 1050 ml of methylene chloride while stirring at between 0° and 5°. Thereafter, ethylene was introduced into the mixture at between 0°-5° during 30 minutes, whereupon the mixture was stirred at room temperature for a further 1 hour and then treated at between 0° and 5° within 3 minutes with 600 ml of ice-water. The methylene chloride phase was washed with 2N hydrochloric acid, water and saturated sodium hydrogen carbonate solution, dried over sodium sulphate and evaporated. The residue was treated with 250 ml of low-boiling petroleum ether, left to stand in a refrigerator overnight and the 6-fluoro 3,4-dihydro-2(1H)-naphthalenone of melting point 50°-60° was filtered off.

(b) 16.7 g of 6-fluoro-3,4-dihydro-2(1H)-naphthalenone were boiled at reflux for 2.5 hours in 200 ml of benzene and 8.4 ml of pyrrolidine in the presence of 0.35 g of anhydrous p-toluenesulphonic acid. The crude 1-(6-fluoro-3,4-dihydro-2-naphthyl)pyrrolidine obtained was, without further purification, treated with 10.8 g of acrylamide and 0.5 g of p-toluenesulphonic acid. The mixture was heated under nitrogen to 100° for 2 hours and to 150° for 2 hours. The reaction mixture was dissolved in 180 ml of chloroform and washed with water. The organic phase was filtered over 150 g of silica gel (particle size 0.2-0.5 mm) while eluting with chloroform. After recrystallization from ethyl acetate there was obtained 8-fluoro-1,4,5,6-tetrahydrobenzo[h]quinolin-3(2H)-one of melting point 223°-224°.

(c) 6.2 g of 8-fluoro-1,4,5,6-tetrahydrobenzo[h]quinolin-3(2H)-one were added portionwise within 35 minutes at between 20° and 25° to a suspension, stirred at 20° under nitrogen, of 2.17 g of lithium aluminum hydride in 60 ml of dry tetrahydrofuran. The reaction mixture was subsequently heated to boiling under reflux for 150 minutes, then cooled and thereupon treated at between 0° and 10° with 7.0 ml of 6.5N sodium hydroxide solution. The resulting suspension was filtered, whereupon the filter residue was rinsed several times with 20 ml of tetrahydrofuran each time and the filtrate was evaporated in vacuo. The thus-obtained 8-fluoro-1,2,3,4,5,6-hexahydrobenzo[f]-quinoline was processed directly.

(d) 6 g of crude 8-fluoro-1,2,3,4,5,6-hexahydrobenzo[f]-quinoline were taken up in 13 ml of pyridine and 12 ml of acetic anhydride. The reaction mixture was left to stand at room temperature for 20 hours, then evaporated, the residue remaining behind was taken up twice in 50 ml of dry toluene each time and the solutions obtained were evaporated to dryness. The residue was dissolved in methylene chloride and chromatographed on 150 g of silica gel (particle size 0.2-0.5 mm). The 4-acetyl-8 fluoro-1,2,3,4,5,6-hexahydrobenzo[f]quinoline, eluted with methylene chloride, exhibits a melting point of 101°-102° after recrystallization from isopropyl ether.

(e) 2.48 g of 4-acetyl-8-fluoro-1,2,3,4,5,6-hexahydrobenzo[f]quinoline were dissolved in 60 ml of chloroform, whereupon 5.24 g of 85% m-chloroperbenzoic acid dissolved in 40 ml of chloroform were added dropwise at 0° to +5°. Thereafter, the mixture was stirred at room temperature for 3 hours. 1.10 g of potassium iodide and 15 ml of water were added and the resulting mixture was treated with sodium thiosulphate until decolorization occured. The chloroform phase was separated and washed with 15 ml of 2N sodium hydroxide solution and 2×40 ml of water. The aqueous extracts were extracted with 20 ml of chloroform. The combined chloroform extracts were dried and evaporated in vacuo. The 4-acetyl-11-fluoro-1,2,4,5,6,7-hexahydro-4-benzazecine-3,8-dione, recrystallized from ethyl acetate, exhibits a melting point of 161°-162°.

EXAMPLE 6

(a) 1155 g (6.4 mol) of 6-chloro-3,4-dihydro-2(1H)-naphthalenone were dissolved in 5 l of toluene, 500 g (7.0 mol) of pyrrolidine and subsequently a solution of 26 g (0.14 mol) of p-toluenesulphonic acid in toluene were added dropwise thereto and the mixture was boiled under reflux When about 120 ml of water had separated, 4 l of toluene were distilled off and the mixture was left to cool slowly. A solid crystallized out. Filtration and washing with acetone gave 1-(6-chloro-3,4-dihydro-2-naphthyl)pyrrolidine of melting point 117°-118°. Concentration of the mother liquor, suspension of the residue in ether, filtration and washing with acetone gave a further portion of the above product of melting point 117°-118°.

(b) 701 g (3 mol) of 1-(6-chloro-3,4-dihydro-2-naphthyl)pyrrolidine and 640 g (19 mol) of acrylamide in 7 ml of ethanol were boiled under reflux for 3 days with the addition of 70 g of Amberlite IR200. The separated solid was filtered off. Extractive crystallization with dioxan gave 8-chloro-1,4,5,6-tetrahydrobenzo[f]-quinolin-3(2H)-one of melting point 228°-230° C.

(c) 147 g (1.94 mol) of lithium aluminum hydride were suspended in 4 l of tetrahydrofuran under argon, 454 g (1.94 mol) of 8-chloro-1,4,5,6-tetrahydrobenzo[f]quinolin-3(2H)-one were slowly added thereto and the mixture was boiled under reflux for 2.5 hours. The mixture was then cooled, 470 ml of 18 percent sodium hydroxide solution were added thereto, the resulting mixture was stirred at room temperature for 30 minutes, filtered and the filter residue was washed with tetrahydrofuran. Upon evaporation of the filtrate there was obtained 8-chloro-1,2,3,4,5,6-hexahydrobenzo[f]quinoline as a yellow oil.

(d) 229 g (1.04 mol) of 8-chloro-1,2,3,4,5,6-hexahydrobenzo[f]quinoline were dissolved in 2 ml of methylene chloride, treated with 115 g (1.14 mol) of triethylamine, and 89.5 g (1.14 mol) of acetyl chloride in 400 ml of methylene chloride were added dropwise thereto at 0°. After stirring at room temperature for 1 hour, the mixture was poured into water, extracted with methylene chloride, and the methylene chloride phase was dried with magnesium sulphate. Distillation of the solvent in vacuo gave a crude product which was suspended in 500 ml of ether and filtered off. There was obtained 4-acetyl-8-chloro-1,2,3,4,5,6-hexahydrobenzo[f]quinoline of melting point 106°–108°. Concentration of the mother liquor and chromatography (silica gel/chloroform) gave a further portion of melting point 106°–108°.

4-Acetyl-8-chloro-1,2,3,4,5,6-hexahydrobenzo[f]quinoline can also be prepared from 6-chloro-3,4-dihydro-2(1H)-naphthalenone as follows:

100 g (0.55 mol) of 6-chloro-3,4-dihydro-2(1H)-naphthalenone were dissolved in 2 l of toluene under argon, treated with 64.0 g of powdered potassium hydroxide, heated to boiling temperature, 165 g of 3-chloropropylamine hydrochloride were added portionwise thereto during 30 minutes and the mixture was boiled on a water separator until educt can no longer be detected in a thin-layer chromatogram. After cooling to room temperature the mixture was treated with 155 ml of triethylamine. The mixture was treated dropwise with 60 ml of acetyl chloride dissolved in 450 ml of toluene while cooling with ice so that an internal temperature of 25° was not exceeded. The mixture was stirred at room temperature for 1 hour, extracted with water/methylene chloride, dried with magnesium sulphate, the solvent was distilled off in vacuo and there was obtained 4-acetyl-8-chloro-1,2,3,4,5,6-hexahydrobenzo[f]quinoline in the form of brown crystals which can be employed as the crude product for the reaction described hereinafter.

(e) 115 g (0.44 mol) of 4-acetyl-8-chloro-1,2,3,4,5,6-hexahydrobenzo[f]quinoline were dissolved in 1 l of methylene chloride and a suspension of 189 g (0.93 mol) of m-chloroperbenzoic acid (85%) in 500 ml of methylene chloride was added dropwise thereto at 0°. After stirring at room temperature for 1 hour the precipitate formed was filtered off and the filtrate was extracted with 2N sodium hydroxide solution and with water. Drying of the organic phase with magnesium sulphate, distillation of the solvent in vacuo and recrystallization of the residue from ethyl acetate-ether gave 4-acetyl-11-chloro-1,2,4,5,6,7-hexahydro-4-benzazecine-3,8-dione as white crystals of melting point 154°–156°.

EXAMPLE 7

(a) 8.40 g (0.038 mol) of 8-chloro-1,2,3,4,5,6-hexahydrobenzo[f]quinoline were dissolved in 20 ml of pyridine and 23.4 g (0.172 mol) of propionic anhydride were added dropwise thereto at 0°. After stirring overnight at room temperature the mixture was extracted with water and ethyl acetate, dried with magnesium sulphate and the solvent was distilled off in vacuo. Chromatography (silica gel, chloroform-hexane 3:1) and crystallization (ethyl acetate) gave 4-propionyl-8-chloro-1,2,3,4,5,6-hexahydrobenzo[f]quinoline as white crystals of melting point 115°–117°.

(b) 7.85 g (0.028 mol) of 4-propionyl-8-chloro-1,2,3,4,5,6-hexahydrobenzo[f]quinoline were dissolved in 80 ml of chloroform and a suspension of 11.6 g (0.058 mol) of 85% m-chloroperbenzoic acid in 100 ml of chloroform was added dropwise thereto at 0°. After stirring at room temperature for 3 hours the mixture was extracted with 2N sodium hydroxide solution and water, dried with magnesium sulphate and the solvent was distilled off in vacuo. Crystallization from ethyl acetate-ether gave 11-chloro-1,2,4,5,6,7-hexahydro-4-propionyl-4-benzazecine-3,8-dione as white crystals of melting point 149°–151°.

EXAMPLE 8

(a) 7.00 g (0.032 mol) of 8-chloro-1,2,3,4,5,6-hexahydrobenzo[f]quinoline Were dissolved in 50 ml of pyridine and 6.75 g (0.048 mol) of benzoyl chloride were added dropwise thereto at 0°. After stirring at room temperature overnight the mixture was extracted with water and chloroform, dried with magnesium sulphate and the solvent was distilled off in vacuo. Chromatography (silica gel, chloroform-hexane, 1:1) and crystallization (chloroform-hexane) gave 4-benzoyl-8-chloro-1,2,3,4,5,6-hexahydrobenzo[f]-quinoline as white crystals of melting point 194°–196°.

(b) 7.80 g (0.024 mol) of 4-benzoyl-8-chloro-1,2,3,4,5,6-hexahydrobenzo[f]quinoline were dissolved in 100 ml of chloroform and a suspension of 9.80 g (0.05 mol) of 85% m-chloroperbenzoic acid in 100 ml of chloroform was added dropwise thereto at 0°. After stirring at room temperature for 3 hours the mixture was extracted with 2N sodium hydroxide solution and water, dried with magnesium sulphate and the solvent was distilled off in vacuo. Chromatography (silica gel, chloroform-hexane, 1:2) and crystallization (ethyl acetate-hexane) gave 4-benzoyl-11-chloro-1,2,4,5,6,7-hexahydro-4-benzazecine-3,8-dione as white crystals of melting point 129°–131°.

EXAMPLE 9

(a) 7.00 g (0.032 mol) of 8-chloro-1,2,3,4,5,6-hexahydrobenzo[f]quinoline were dissolved in 50 ml of pyridine and 7.42 g (0.048 mol) of phenylacetyl chloride were added dropwise thereto at 0°. After stirring overnight at room temperature the mixture was poured into water, extracted with ethyl acetate, dried with magnesium sulphate and the solvent was distilled off in vacuo. Chromatography (silica gel, chloroform-hexane, 1:1) gave 8-chloro-4-(phenylacetyl)-1,2,3,4,5,6-hexahydrobenzo[f]quinoline in the form of an oil.

(b) 7.10 g (0.021 mol) of 8-chloro-4-(phenylacetyl)-1,2,3,4,5,6-hexahydrobenzo[f]quinoline were dissolved in 100 ml of chloroform and a suspension of 8.55 g (0.043 mol) of 85% m-chloroperbenzoic acid in 100 ml of chloroform was added dropwise thereto at 0°. After stirring at room temperature for 3 hours the mixture was extracted with 2N sodium hydroxide solution and water, dried with magnesium sulphate and the solvent was distilled off in vacuo. Chromatography (silica gel, chloroform-hexane, 1:1) and crystallization (ethyl acetate-hexane) gave 11-chloro-1,2,4,5,6,7-hexahydro-4-(phenylacetyl)-4-benzazecine-3,8-dione as white crystals of melting point 178°–180°.

EXAMPLE 10

26.3 g (0.12 mol) of B-chloro-1,2,3,4,5,6-hexahydrobenzo[f]quinoline dissolved in 3 l of methylene chloride were added to a solution of 4.75 g (0.03 mol) of potassium permanganate and 514 g (2.4 mol) of sodium periodate in 12 l of water, 3.00 g (0.013 mol) of benzyltriethylammonium chloride were added thereto and the mixture wad stirred at room temperature overnight. The mixture was filtered over Dicalit and extracted with methylene chloride. Drying with sodium sulphate, distillation of the solvent in vacuo and chromatography (silica gel, ethyl acetate) gave 11-chloro-1,2,4,5,6,7-hexahydro-4-benzazecine-3,8-dione as beige crystals of melting point 142°–144°.

EXAMPLE 11

A solution of 2.05 g (7 mmol) of 4-acetyl-11-chloro-1,2,4,5,6,7-hexahydro-4-benzazecine-3,8-dione in 30 ml of methanol was treated with 0.85 g (15.4 mmol) of sodium methanolate, stirred at room temperature for 2 hours, the reaction mixture was concentrated in vacuo, treated with water and extracted at pH 14 with chloroform. After drying the chloroform phase with sodium sulphate and distillation of the solvent in vacuo there was obtained 11-chloro- 1,2,4,5,6,7-hexahydro 4-benzazecine-3,8-dione of melting point 142°–144°.

EXAMPLE 12

(a) 15.0 g (0.06 mol) of 8-chloro-1,2,3,4,5,6-hexahydrobenzo[f]quinoline were dissolved in 150 ml of methylene chloride, treated with 6.68 g (0.066 mol) of triethylamine and 11.2 g (0.066 mol) of p-methoxybenzoyl chloride in 50 ml of methylene chloride were added dropwise thereto at 0°. After stirring at room temperature for 1 hour the mixture was extracted with water, dried with magnesium sulphate and the solvent was distilled off in vacuo. Crystallization (methylene chloride-ether) gave 4-(p-methoxybenzoyl)-8 -chloro-1,2,3,4,5,6-hexahydrobenzo[f]quinoline as white crystals of melting point 182°–183°.

(b) 8.80 g (0.025 mol) of 4-(p-methoxybenzoyl)-8-chloro-1,2,3,4,5,6-hexahydrobenzo[f]quinoline were dissolved in 100 ml of chloroform and a suspension of 10.3 g (0.051 mol) of 85% m-chloroperbenzoic acid in 100 ml of chloroform was added dropwise thereto at 0°. After stirring at room temperature for 1 hour the mixture was extracted with 2N sodium hydroxide solution and water, dried with magnesium sulphate and the solvent was distilled off in vacuo. Chromatography (silica gel, ether-hexane, 2:1) and crystallization (ether-hexane) gave 4-(p-methoxybenzoyl)-11-chloro-1,2,4,5,6,7 -hexahydro-4-benzazecine-3,8-dione as white crystals of melting point 143°.

EXAMPLE 13

(a) 8.78 g (40 mmol) of 8-chloro-1,2,3,4,5,6-hexahydrobenzo[f]quinoline were dissolved in 88 ml of methylene chloride and 7.70 g (44 mmol) of 4-chlorobenzoyl chloride in 60 ml of methylene chloride were added dropwise thereto at 0°. After stirring at room temperature for 1 hour the mixture was extracted with water, dried with magnesium sulphate and the solvent was distilled off in vacuo. Chromatography (silica gel, chloroform-hexane, 2:1) and crystallization (chloroform-hexane) gave 8-chloro-4 (p-chlorobenzoyl)-1,2,3,4,5,6 -hexahydrobenzo[f]quinoline as white crystals of melting point 189°–191°.

(b) 5.20 g (14.5 mmol) of 8-chloro-4-(p-chlorobenzoyl)-1,2,3,4,5,6 -hexahydrobenzo[f]quinoline were dissolved in 50 ml of chloroform and a suspension of 5.90 g (29 mmol) of 85% m-chloroperbenzoic acid in 50 ml of chloroform was added dropwise thereto at 0°. After stirring at room temperature for 1 hour the mixture was extracted with 2N sodium hydroxide solution and water, dried with magnesium sulphate and the solvent was distilled off in vacuo. Chromatography (silica gel, chloroform) and crystallization (ether-hexane) gave 11-chloro-4-(p-chlorobenzoyl)-1,2,4,5,6,7-hexahydro-4-benzazecine-3,8-dione as white crystals of melting point 141°–143°.

EXAMPLE 14

(a) 14.3 g (0.066 mol) of 8-chloro-1,2,3,4,5,6-hexahydrobenzo[f]quinoline were dissolved in 143 ml of methylene chloride, treated with 6.68 g (0.066 mol) of triethylamine and 11.3 g (0.066 mol) of m-methoxybenzoyl chloride in 60 ml of methylene chloride were added dropwise thereto at 0°. After stirring at room temperature for 1 hour the mixture was extracted with water, dried with magnesium sulphate and the solvent was distilled off in vacuo. Chromatography (silica gel, toluene-ethyl acetate, 19:1) and crystallization (methylene chloride-ether) gave 4-(m-methoxybenzoyl)-8-chloro-1,2,3,4,5,6-hexahydrobenzo[f]quinoline as white crystals of melting point 133°.

(b) 3.20 g (0.009 mol) of 4-(m-methoxybenzoyl)-8 chloro-1,2,3,4,5,6 -hexahydrobenzo[f]quinoline were dissolved in 35 ml of methylene chloride and a suspension of 3.77 g (0.019 mol) of 85 percent m-chloroperbenzoic acid in 35 ml of methylene chloride was added dropwise thereto at 0°. After stirring at room temperature for 1 hour the mixture was extracted with 2N sodium hydroxide solution and water, dried with magnesium sulphate and the solvent was distilled off in vacuo. Crystallization (methylene chloride-ether) gave 4-(m-methoxybenzoyl)-11-chloro-1,2,4,5,6,7-hexahydro-4-benzazecine-3,8-dione as white crystals of melting point 105°–106°.

EXAMPLE 15

(a) 5.00 g (0.02 mol) of 8-chloro-1,2,3,4,5,6-hexahydro[f]quinoline were dissolved in 70 ml of methylene chloride, treated with 2.23 g (0.022 mol) of triethylamine and 3.85 g (0.022 mol) of o-methoxybenzoyl chloride in 20 ml of methylene chloride were added dropwise thereto at 0°. After stirring at room temperature for 1 hour the mixture was extracted with water, dried with magnesium sulphate and the solvent was distilled off in vacuo. Chromatography (silica gel, toluene-ethyl acetate, 9:1) and crystallization (methylene chloride-ether) gave 4-(o-methoxybenzoyl)-8-chloro-1,2,3,4,5,6-hexahydrobenzo[f]quinoline as white crystals of melting point 139°.

(b) 5.75 g (0.016 mol) of 4-(o-methoxybenzoyl)-8-chloro-1,2,3,4,5,6-hexahydrobenzo[f]quinoline were dissolved in 60 ml of methylene chloride and a suspension of 6.70 g (0.033 mol) of 85 percent m-chloroperbenzoic acid in 60 ml of methylene chloride was added dropwise thereto at 0°. After stirring at room temperature for 1 hour the mixture was extracted with 2N sodium hydroxide solution and water, dried with magnesium sulphate and the solvent was distilled off in vacuo. Crystallization (methylene chloride-ether) gave 4-(o-methoxybenzoyl)-11-chloro- 1,2,4,5,6,7-hexahydro 4 benzazecine 3,8-dione as white crystals of melting point 179°.

EXAMPLE 16

(a) 96.9 g of p-bromophenylacetyl chloride dissolved in 200 ml of methylene chloride were added dropwise within 50 minutes to 110.7 g of aluminum chloride in 800 ml of methylene chloride while stirring at between 0° and 5°. Thereafter, ethylene was introduced into the mixture at between 0°–5° during 30 minutes, whereupon the resulting mixture was stirred at room temperature for a further 1 hour and then 600 ml of cold water were added thereto at between 0° and 3°. The methylene chloride phase was separated and washed with 2×350 ml of 2N hydrochloric acid and 2×350 ml of saturated sodium bicarbonate solution. The aqueous phases were extracted with 200 ml of methylene chloride. The combined methylene chloride extracts were dried over sodium sulphate and concentrated in vacuo. The 6-bromo-3,4-dihydro-2(1H)-naphthalenone, crystallized-out from 400 ml of low-boiling petroleum ether, exhibits a melting point of 75°–77°.

(b) 35.0 g of 6-bromo-3,4-dihydro-2(1H)-naphthalenone were boiled at reflux for 3 hours in 250 ml of benzene and 12.5 ml of pyrrolidine in the presence of 0.5 g of p-toluenesulphonic acid. After evaporation of the toluene in vacuo the residue was triturated in diethyl ether. The crystallized-out 1-(6-bromo-3,4-dihydro-2-naphthyl)pyrrolidine exhibits a melting point of 125°–127°. A further portion of the above product of melting point 127°–128° can be isolated from the mother liquor by trituration in isopropyl ether.

(c) 17.5 g of acrylamide and 0.65 g of p-toluenesulphonic acid were added to 35.5 g of 1-(6-bromo-3,4-dihydro-2-naphthyl)pyrrolidine. The mixture was heated under nitrogen to 100° for 2 hours and to 150° for 2 hours. The reaction mixture was treated with 250 ml of chloroform. whereupon the insoluble constituents were filtered off. There was obtained 8-bromo-1,4,5,6-tetrahydrobenzo[f]-quinolin-3(2H)-one of melting point 227°–228°. After recrystallization from ethanol the product exhibits a melting point of 230°–231°.

(d) 19.0 g of 8-bromo-1,4,5,6-tetrahydrobenzo[f]quinolin-3(2H)-one were added portionwise within 35 minutes at between 20° and 25° to a suspension, stirred at 20° under nitrogen, of 5.2 g of lithium aluminum hydride in 140 ml of dry tetrahydrofuran. The reaction mixture was subsequently heated to boiling under reflux for 150 minutes, then cooled and thereupon treated at between 0° and 10° with 17 ml of 6.5N sodium hydroxide solution. The resulting suspension was filtered, whereupon the filter residue was rinsed several times with tetrahydrofuran and the filtrate was evaporated in vacuo. The thus-obtained 8-bromo-1,2,3,4,5,6-hexahydrobenzo[f]quinoline was processed directly.

(e) 13.9 g of crude 8-bromo-1,2,3,4,5,6-hexahydrobenzo[f]quinoline were taken up in 29 ml of pyridine and 27.0 ml of acetic anhydride. The reaction mixture was left to stand at room temperature for 20 hours, evaporated, the residue remaining behind was taken up twice in 100 ml of dry toluene each time and the solutions obtained were evaporated to dryness. The residue was dissolved in ethyl acetate and chromatographed on 200 g of silica gel (particle size 0.2–0.5 mm). The 4-acetyl-8-bromo-1,2,3,4,5,6-hexahydrobenzo[f]quinoline, eluted with ethyl acetate, exhibits a melting point of 96°–97° after recrystallization from isopropyl ether.

(f) 8.0 q of 4-acetyl-8-bromo-1,2,3,4,5,6-hexahydrobenzo[f]quinoline were dissolved in 80 ml of chloroform. whereupon 11.2 g of 85% m-chloroperbenzoic acid dissolved in 80 ml of chloroform were added dropwise at between 0° and +5°. Thereafter, the mixture was stirred at room temperature for 4 hours, whereupon 1.0 g of potassium iodide and 200 ml of water were added thereto and the mixture was then treated with sodium thiosulphate until decolorization occurred. The chloroform phase was separated and washed With 100 ml of 2N sodium hydroxide solution and with 200 ml of water. The aqueous phases were extracted with 100 ml of chloroform. The combined chloroform extracts were dried and evaporated in vacuo. The 4-acetyl-11-bromo-1,2,4,5,6,7-hexahydro-4-benzazecine-3,8-dione, recrystallized from ethyl acetate, exhibits a melting point of 162°–164°.

EXAMPLE 17

(a) 12.0 g of 6-methoxy-2-tetralone were boiled at reflux for 2 hours in 200 ml of benzene and 5.6 ml of pyrrolidine, in the presence of 0.5 g of anhydrous p-toluenesulphonic acid. The toluene was removed in vacuo. 9.70 g of acrylamide and 0.5 g of p-toluenesulphonic acid were added to the thus-obtained crude 1-(6-methoxy-3,4-dihydro-2-naphthyl)pyrrolidine. The mixture was heated under nitrogen to 100° for 2 hours and to 150° for 2 hours. The reaction mixture was partitioned between 400 ml of chloroform and 40 ml of water. The organic phase was washed with 2×40 ml of water and the aqueous phases were extracted with 1×100 ml of chloroform. The chloroform phases were combined, dried over sodium sulphate and concentrated. The residue was chromatographed on 160 g of silica gel (particle size 0.2–0.5 mm). The 8-methoxy-1,4,5,8-tetrahydrobenzo[f]quinolin-3(2H)-one, eluted with methylene chloride and recrystallized from ethyl acetate, exhibits a melting point of 208°–209°.

(b) 5.1 g of 8-(methoxy-1,4,5,8-tetrahydrobenzo[f]-quinolin-3(2H)-one were added portionwise within 35 minutes at between 20° and 25° to a suspension, stirred at 20° under nitrogen, of 1.69 g of lithium aluminum hydride in 50 ml of dry tetrahydrofuran. The reaction mixture was subsequently heated to boiling under reflux for 150 minutes, then cooled and thereupon treated at between 0° and 10° with 1.5 ml of 6.5N sodium hydroxide solution. The resulting suspension was filtered, whereupon the filter residue was rinsed several times with tetrahydrofuran and the filtrate was evaporated in vacuo. The thus-obtained 8-methoxy-1,2,3,4,5,6-hexahydrobenzo[f]quinoline was processed directly.

(c) 4.7 g of 8-methoxy-1,2,3,4,5,6-hexahydrobenzo[f]quinoline were taken up in 15 ml of pyridine and 11 ml of acetic anhydride. The reaction mixture was left to stand at room temperature for 20 hours, then evaporated, the residue remaining behind was taken up twice in 50 ml of dry toluene each time and the solutions obtained were evaporated to dryness. The residue was dissolved in methylene chloride and chromatographed on 50 g of silica gel (particle size 0.2–0.5 mm). The 4-acetyl-8-methoxy-1,2,3,4,5,6-hexahydrobenzo[f]quinoline, eluted with methylene chloride, exhibits a melting point of 119°–120° after recrystallization from isopropyl ether.

(d) 21.3 g of 4-acetyl-8-methoxy-1,2,3,4,5,6-hexahydrobenzo[f]quinoline were dissolved in 200 ml of chloroform, whereupon 38.0 g of 85% m-chloroperbenzoic acid dissolved in 250 ml of chloroform were added dropwise at 0° to +5°. Thereafter, the mixture was stirred at room temperature for 18 hours, whereupon sodium iodide and water were added and thereafter the mixture was treated with sodium thiosulphate until decolorization occurred. The chloroform phase was washed with aqueous ammonia and sodium chloride solution. The aqueous phases were extracted with chloroform. The combined chloroform extracts were dried over sodium sulphate and evaporated in vacuo. The 4-acetyl-11-methoxy-1,2,3,4,5,6,7-hexahydro-4-benzazecine-3,8-dione, recrystallized from ethyl acetate. exhibits a melting point 156°–158°.

EXAMPLE 18

(a) 20.6 g of 5-chloro-1-tetralone were dissolved in 100 ml of alcohol, whereupon 2.2 g of sodium borohydride were added portionwise. The reaction mixture was stirred at 40° for 2 hours, then cooled and thereupon treated at room temperature with 32 ml of 2N hydrochloric acid. The mixture was then concentrated in vacuo and extracted with methylene chloride. The organic phases were dried over sodium sulphate and evaporated. The 5-chloro-1-tetralol which remains behind as the residue was processed directly as the crude product.

(b) 20.6 g of crude 5-chloro-1-tetralol were dissolved in 400 ml of toluene and 1.60 g of p-toluenesulphonic acid were added to this solution. The mixture was heated at reflux for 2 hours, whereby 1.9 ml of water were collected with a water separator. Thereupon, 3 g of molecular sieve 4A were added thereto and the mixture was heated at reflux for a further 30 minutes. The reaction mixture was cooled; the organic phase was washed once with 100 ml of saturated aqueous sodium bicarbonate solution and twice with 50 ml of water each time, dried and evaporated in vacuo. The 5-chloro-3,4-dihydronaphthalene which remained behind as the residue was distilled in a bulb-tube; boiling point 100°/0.05mmHg.

(c) 17.0 g of 5-chloro-3,4-dihydro-naphthalene dissolved in 300 ml of methylene chloride were added dropwise within 20 minutes at between 0° and +5° to 23.2 g of m-chloroperbenzoic acid (85%) dissolved in 320 ml of methylene chloride. The mixture was subsequently stirred at room temperature for 3.5 hours and then washed six times with 100 ml of 5% aqueous ammonia each time. The methylene chloride phase was dried over sodium sulphate, filtered and evaporated in vacuo. The 5-chloro-oxirano[α]-2,3-dihydronaphthalene which remained behind as the residue was processed as the crude product.

(d) 24 g of crude 5-chlorooxirano[α]-2,3-dihydronaphthalene were dissolved in 350 ml of toluene. To this solution was added dropwise under nitrogen at room temperature a freshly prepared magnesium bromide solution (4.25 g of magnesium shavings were treated in 800 ml of diethyl ether under nitrogen with 8.2 ml (25.5 g) of bromine, whereupon the mixture was boiled for 30 minutes and decanted off from the insoluble constituents). The mixture was subsequently stirred at room temperature for 1 hour. The diethyl ether was distilled off in vacuo and replaced continuously by 1000 ml of toluene. The mixture obtained was boiled under reflux for 2 hours, cooled to room temperature and then washed with 300 ml of cold water and with 2×100 ml of cold water each time. The aqueous phases were back-extracted with 150 ml of toluene. The combined organic phases were dried over sodium sulphate and concentrated. The residue was chromatographed over 100 g of silica gel (particle size 0.04–0.063 mm). The 5-chloro-2-tetralone, eluted with toluene, was distilled in a bulb-tube for further purification (boiling point 145°–150°/0.04mmHg). The crystallized product exhibits a melting point of 32°–34° (sintering from 31°).

(e) 11.07 g of 5-chloro-2-tetralone were boiled at reflux for 2 hours in 200 ml of benzene and 10.1 ml of pyrrolidine in the presence of 0.3 g of p-toluenesulphonic acid. The crude 1-(5-chloro-3,4-dihydro-2-naphthyl)pyrrolidine obtained was treated, without purification, with 9.0 g of acrylamide and 0.5 g of p-toluenesulphonic acid. The mixture was heated under nitrogen to 100° for 2 hours and to 150° for 2 hours. 250 ml of ethyl acetate and 50 ml of water were added to the reaction mixture, whereupon the insoluble constituents were filtered off, washed with ethyl acetate and water, dried and recrystallized from ethyl acetate. There was obtained 7-chloro-1,2,5,6-tetrahydrobenzo[f]quinolin-3(4H)-one of melting point 252°–253°.

(f) 4.0 g of 7-chloro-1,2,5,6-tetrahydrobenzo[f]quinolin-3(4H)-one were added portionwise within 35 minutes at between 20° and 25° to a suspension, stirred under nitrogen, of 1.30 g of lithium aluminum hydride in 60 ml of dry tetrahydrofuran. The reaction mixture was subsequently heated to boiling under reflux for 150 minutes, then cooled and thereupon treated at between 0° and 10° with 4.2 ml of 6.5N sodium hydroxide solution. The resulting suspension was filtered, whereupon the filter residue was rinsed with 5×20 ml of tetrahydrofuran each time and the filtrate was evaporated in vacuo. The thus-obtained crude 7-chloro-1,2,3,4,5,6-hexahydrobenzo[f]-quinoline was taken up in 10 ml of pyridine and 9.0 ml of acetic anhydride. The reaction mixture was left to stand at room temperature for 20 hours, evaporated, the residue remaining behind was taken up twice in 50 ml of dry toluene and the solutions obtained were evaporated to dryness. The residue was dissolved in methylene chloride and chromatographed on 70 g of silica gel (particle size 0.04–0.063 mm). The 4-acetyl-7-chloro-1,2,3,4,5,6-hexahydrobenzo[f]quinoline, eluted with chloroform, exhibits a melting point of 89°–90° after recrystallization from isopropyl ether.

(g) 3.4 g of 4-acetyl-7-chloro-1,2,3,4,5,6-hexahydrobenzo-[f]quinoline were dissolved in 100 ml of chloroform. whereupon 6.8 g of 85% m-chloroperbenzoic acid dissolved in 100 ml of chloroform were added dropwise at 0° to +5°. After stirring at room temperature for 3 hours, 1.5 g of potassium iodide and 40 ml of water were added, whereupon the mixture was treated with sodium thiosulphate until decolorization occurred. The chloroform phase was washed with 40 ml of 2N sodium hydroxide solution and 2×80 ml of water. The aqueous phases were extracted with 100 ml of chloroform. The combined chloroform extracts were dried and evaporated in vacuo. The 4-acetyl-12-chloro-1,2,4,5,6,7-hexahydro-4-benzazecine-3,8-dione, recrystallized from ethyl acetate, exhibits a melting point of 160°–162°.

EXAMPLE 19

(a) 75.0 g of 5-methoxy-1-tetralone were dissolved in 1125 ml of ethanol, whereupon 8.05 g of sodium borohydride were added at room temperature. The reaction mixture was warmed to 40° for 3.5 hours, then cooled to room temperature and thereupon treated at 20°–26° with 120 ml of 2N hydrochloric acid. The mixture was then concentrated in vacuo and extracted with methylene chloride. The organic phases were dried over sodium sulphate and evaporated. The 1,2,3,4-tetrahydro-5-methoxy-1-naphthalenol which remained behind as the residue exhibits a melting point of 78.5°–79° after recrystallization from n hexane.

(b) 51.0 g of 1,2,3,4-tetrahydro-5-methoxy-1-naphthalenol were boiled for 2 hours in 1.7 l of toluene with 4.0 g of p-toluenesulphonic acid on a water separator. The reaction mixture was washed with 200 ml of saturated sodium bicarbonate solution and with 2×200 ml of water. The toluene phase was dried over sodium sulphate and evaporated in vacuo, whereby crude 7,8- dihydro-1-naphthyl methyl ether remained behind as the residue. For purification, the crude product obtained was chromatographed over 600 g of silica gel (particle size 0.2–0.5 mm). The 7,8-dihydro-1-naphthyl methyl ether, eluted with n-hexane, was processed directly without further purification. A sample which was distilled in a bulb-tube exhibits a boiling point of 110°/0.05 mmHg.

(c) 36 g of 7,8-dihydro-1-naphthyl methyl ether dissolved in 600 ml of methylene chloride were added dropwise to -50.3 g of 85% m-chloroperbenzoic acid in 800 ml of methylene chloride at between 0° and +5°. The mixture was subsequently stirred at room temperature for 5.5 hours and then washed with 6×200 ml of 5% aqueous ammonia. The aqueous phases were extracted with 300 ml of methylene chloride. The organic phases were combined, dried over sodium sulphate and concentrated. The thus-obtained 5-methoxyoxirano[a]-2,3-dihydronaphthalene was, without previous purification, dissolved in 800 ml of toluene. To this solution there was added dropwise under nitrogen at room temperature a freshly prepared magnesium bromide solution (9.2 g of magnesium shavings were treated in 1.7 l of diethyl ether under nitrogen with 17.8 ml (55.2 g) of bromine, whereupon the mixture was boiled for 30 minutes and decanted off from the insoluble constituents). The mixture was subsequently stirred at room temperature for 1 hour. The diethyl ether was distilled off in vacuo and replaced continuously by 2 l of toluene. The solution obtained was boiled under reflux for 3 hours, then cooled to room temperature and washed with 3×200 ml of cold water, whereupon the aqueous phases were extracted with 300 ml of toluene. The organic phases were combined, dried over sodium sulphate and concentrated. The residual crude 3,4-dihydro-5-methoxy-2-(1H)-naphthalenone was chromatographed over 500 g of silica gel (particle size 0.2–0.5 mm). The product, eluted with toluene, was distilled in a bulb-tube for further purification and exhibits a melting point of 37.5°–38.5°.

(d) 10.18 g of 3,4-dihydro-5-methoxy-2(1H)-naphthalenone were boiled at reflux for 2 hours in 200 ml of benzene and 4.8 ml of pyrrolidine in the presence of 0.25 g of p-toluenesulphonic acid. The toluene was distilled off in vacuo and the residue was triturated in low-boiling petroleum ether. The 1-(5-methoxy-3,4-dihydro-2-naphthyl)pyrrolidine was filtered off and exhibits a melting point of 77°–78°.

(e) 7.3 g of acrylamide and 0.4 g of p-toluenesulphonic acid were added to 9.9 g of 1-(5-methoxy-3,4-dihydro-2-naphthyl)pyrrolidine. The mixture was heated under nitrogen to 100° for 2 hours and to 150° for 2 hours, and then 150 ml of chloroform and 30 ml of water were added thereto. The separated 1,4,5,6-tetrahydro-7-methoxy-3(2H)-quinolinone was filtered off and exhibits a melting point of 248°–250°.

(f) 9.1 g of 1,4,5,6-tetrahydro-7-methoxy-3(2H)-quinolinone were added portionwise within 35 minutes at between 20° and 25° to a suspension, stirred at 20° under nitrogen, of 3.1 g of lithium aluminum hydride in 120 ml of dry tetrahydrofuran. The reaction mixture was subsequently heated to boiling under reflux for 150 minutes, then cooled and thereupon treated at between 0° and 10° with 9.7 ml of 6.5N sodium hydroxide solution. The resulting suspension was filtered, whereupon the filter residue was rinsed several times with 20 ml of tetrahydrofuran each time and the combined filtrates were evaporated in vacuo. The thus-obtained 1,2,3,4,5,6-hexa-hydro-7-methoxybenzo[f]quinoline was processed directly.

(g) 9.0 g of 1,2,3,4,5,6-hexahydro-7-methoxybenzo[f]-quinoline were taken up in 20 ml of pyridine and 17.5 ml of acetic anhydride. The mixture was left to stand at room temperature for 20 hours, then evaporated, the residue remaining behind was taken up twice in 75 ml of dry toluene each time and the solutions obtained were evaporated to dryness. The residue was dissolved in ethyl acetate and chromatographed on 100 g of silica gel (particle size 0.2–0.5 mm). The 4-acetyl-1,2,3,4,5,6-hexahydro-7-methoxybenzo[f]quinoline, eluted with ethyl acetate and recrystallized from isopropyl ether, exhibits a melting point of 128°–130°.

(h) 4.87 g of 4-acetyl-1,2,3,4,5,6-hexahydro-7-methoxybenzo[f]quinoline were dissolved in 120 ml of chloroform, whereupon 9.55 g of 85% m-chloroperbenzoic acid dissolved in 120 ml of chloroform were added dropwise at 0° to +5°. Thereafter, the mixture was stirred at room temperature for 3 hours, whereupon 1.6 g of potassium iodide and 40 ml of water were added thereto and the resulting mixture was then treated with sodium thiosulphate until decolorization occurred. The chloroform phase was washed with 40 ml of 2N sodium hydroxide solution and 2×100 ml of water. The aqueous phases were extracted with 100 ml of chloroform. The combined chloroform extracts were dried and evaporated in vacuo. The residue was chromatographed on 60 g of silica gel (particle size 0.2–0.5 mm). The 4-acetyl-1,2,4,5,6,7-hexahydro-12-methoxy-4-benzazecine-3,8-dione, eluted with methylene chloride and recrystallized from ethyl acetate, exhibits a melting point of 170°–172°.

EXAMPLE 20

(a) 149.4 g of 2,4-dichlorophenylacetyl chloride dissolved in 200 ml of methylene chloride were added dropwise within 60 minutes to 115 g of aluminum chloride in 700 ml of methylene chloride while stirring at 0° to 5°. Thereafter, ethylene was introduced at between 0° and 5° during 30 minutes, whereupon the mixture was stirred further at room temperature for 1 hour and thereafter treated at between 0° and 5° with 300 ml of ice-water. The methylene chloride phase was washed, respectively, with 2N hydrochloric acid, with water, with saturated sodium bicarbonate solution and again with water. The aqueous phases were extracted with methylene chloride. The methylene chloride phases were combined, dried and evaporated. The residue was triturated with 100 ml of low-boiling petroleum ether, a further 250 ml of low-boiling petroleum ether were later added thereto and the mixture was left to stand in a refrigerator for 72 hours. The solid was filtered off and filtered over 600 g of silica gel (particle size 0.2–0.5 mm) while eluting with chloroform. There was obtained 6,8-dichloro-3,4-dihydro-2(1H)-naphthalenone which exhibits a melting point of 90°–92° after recrystallization from low-boiling petroleum ether at 0° to 5°.

(b) 30.0 g of 6,8-dichloro-3,4-dihydro-2(1H)-naphthalenone were boiled at reflux for 2 hours in 250 ml of benzene and 11.5 ml of pyrrolidine in the presence of 0.5 g of anhydrous p-toluenesulphonic acid. For purification, the 1-(6,8-dichloro-3,4-dihydro-2-naphthyl)pyrrolidine obtained was triturated with 150 ml of isopropyl ether. The filtered-off solid exhibits a melting point of 84°–86°. A further portion of melting point 84.5°–85.5° can be isolated from the mother liquors. The two portions were combined and, after recrystallization from isopropyl ether, there was obtained 1-(6,8-dichloro-3,4-dihydro-2-naphthyl)pyrrolidine of melting point 85.5°–86°.

(c) 16.2 g of acrylamide and 0.9 g of anhydrous p-toluenesulphonic acid were added to 30.6 g of 1-(6,8-dichloro-3,4-dihydro-2(1H)-naphthyl)pyrrolidine. The mixture was heated under nitrogen to 100° for 2 hours and to 150° for 2 hours. After cooling, the reaction mixture was stirred at room temperature in 80 ml of a mixture of chloroform-ethyl acetate (1:1). There was obtained 8,10-dichloro-1,4,5,6-tetrahydrobenzo[f]quinolin-3(2H)-one which melts at 212°–214° after recrystallization from ethyl acetate.

(d) 8.0 g of 8,10-dichloro-1,4,5,6-tetrahydrobenzo[f]quinolin-3(2H)-one were added portionwise within 35 minutes at between 20°–25° to a suspension, stirred at 20° under nitrogen, of 2.26 g of lithium aluminum hydride in 67 ml of dry tetrahydrofuran. The reaction mixture was subsequently heated to boiling under reflux for 150 minutes, thereafter cooled and treated at between 0° and +10° with 7.38 ml of 6.5N sodium hydroxide solution. The resulting suspension was filtered and the filtrate was evaporated in vacuo. The thus-obtained 8,10-dichloro-1,2,3,4,5,6-hexahydrobenzo[f]quinoline was taken up in 16 ml of pyridine and 14 ml of acetic anhydride, left to stand at room temperature overnight, evaporated, the residue remaining behind was taken up twice in 50 ml of toluene each time and the solutions obtained were evaporated to dryness. The residue was dissolved in chloroform and chromatographed on 100 g of silica gel (particle size 0.2–0.5 mm). The 4-acetyl-8,10-dichloro-1,2,3,4,5,6-tetrahydrobenzo[f]quinoline, eluted with chloroform, exhibits a melting point of 99°–101° after recrystallization from isopropyl ether.

(e) 4.2 g of 4-acetyl-8,10 -dichloro-1,2,3,4,5,6-tetrahydrobenzo[f]quinoline were dissolved in 80 ml of chloroform, whereupon 7.45 g of 85% m-chloroperbenzoic acid dissolved in 80 ml of chloroform were added dropwise at 0° to +5°. Therafter, the mixture was stirred at room temperature for 3 hours, whereupon 1.5 g of potassium iodide and 50 ml of water were added and the resulting mixture was treated with sodium thiosulphate until decolorization occurred. The chloroform phase was washed with 40 ml of 2N sodium hydroxide solution and 2×100 ml of water. The aqueous phases were extracted with 100 ml of chloroform. The combined chloroform extracts were dried and evaporated in vacuo. The 4-acetyl-9,11-dichloro-1,2,4,5,6,7-hexahydro-4-benzazecine-3,8-dione, recrystallized from isopropyl ether, exhibits a melting point of 152°–153°.

EXAMPLE A

Tablets of the following composition, which contains 4-acetyl-11 -chloro-1,2,4,5,6,7-hexahydro-4-benzazecine-3,8-dione as the active substance, are prepared:

| Ingredients | Amt. Per tablet |
|---|---|
| 1. Active substance (micronized) | 50 mg |
| 2. Lactose | 120 mg |
| 3. Maize starch | 50 mg |
| 4. Polyvinylpyrrolidone | 8 mg |
| 5. Sodium carboxymethylstarch | 20 mg |
| 6. Magnesium stearate | 2 mg |
| Total | 250 mg |

PROCEDURE

The active substance is mixed homogeneously with a mixture of lactose and maize starch. The mixture is sieved, moistened with an aqueous polyvinylpyrrolidone solution, granulated and dried. The dried granulate is mixed with sodium carboxymethylstarch and magnesium stearate and the thus-obtained mixture is pressed into tablets of suitable size with a break-bar.

EXAMPLE B

Tablets of the following composition, which contains 4-acetyl-11-chloro-1,2,4,5,6,7-hexahydro-4-benzazecine-3,8-dione as the active substance, are prepared:

| Ingredients | Amt. Per tablet |
|---|---|
| 1. Active substance (micronized) | 10 mg |
| 2. Lactose | 88 mg |
| 3. Microcrystalline cellulose | 60 mg |
| 4. Maize starch | 20 mg |
| 5. Sodium carboxymethylstarch | 20 mg |
| 6. Magnesium stearate | 2 mg |
| Total | 200 mg |

PROCEDURE

The active substance is mixed homogeneously with the lactose. The mixture is sieved, a mixture of microcrystalline cellulose, maize starch and sodium carboxymethylstarch is then admixed therewith and the resulting mixture is blended with the magnesium stearate. The thus-obtained ready-to-press mixture is processed to tablets of suitable size with a break-bar.

We claim:

1. A pharmaceutical composition which comprises a compound of the formula

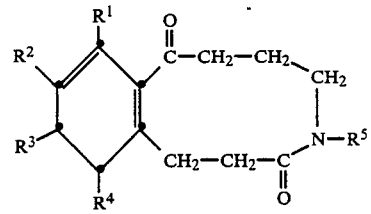

wherein $R^1$ and $R^2$ are independently hydrogen or chlorine, $R^3$ is hydrogen, fluorine, chlorine, bromine or methoxy, $R^4$ is hydrogen, chlorine or methoxy, and $R^5$ is hydrogen, acetyl, propionyl, benzoyl, chlorobenzoyl, methoxybenzoyl or phenylacetyl, with the proviso that 2 or 3 of the groups $R^1$ to $R^4$ are hydrogen, and a therapeutically inert excipient.

2. A pharmaceutical composition which comprises a compound selected from the group consisting of 4-acetyl-8-chloro-1,2,3,4,5,6-hexahydrobenzo[f]-quinoline;
4-acetyl-10-chloro-1,2,3,4,5,6-hexahydrobenzo[f]-quinoline and
8-chloro-4-(p-chlorobenzoyl)-1,2,3,4,5,6-hexahydrobenzo[f]quinoline; and a therapeutically inert excipient.

3. A method of controlling cerebral insufficiency, comprising administering to a mammal an effective amount of a compound of the formula

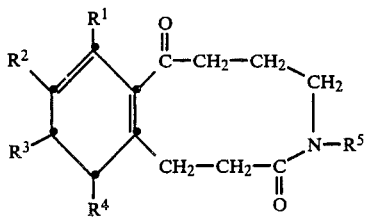

wherein $R^1$ and $R^2$ are independently hydrogen or chlorine, $R^3$ is hydrogen, fluorine, chlorine, bromine or methoxy, $R^4$ is hydrogen, chlorine or methoxy, and $R^5$ is hydrogen, acetyl, propionyl, benzoyl, chlorobenzoyl, methoxybenzoyl or phenylacetyl, with the proviso that 2 or 3 of the groups $R^1$ to $R^4$ are hydrogen.

4. A method of controlling cerebral insufficiency, comprising administering to a mammal an effective amount of a compound selected from the group consisting of
4-acetyl-8-chloro-1,2,3,4,5,6-hexahydrobenzo[f]-quinoline;
4-acetyl-10-chloro-1,2,3,4,5,6-hexahydrobenzo[f]-quinoline and
8-chloro-4-(p-chlorobenzoyl)-1,2,3,4,5,6-hexahydrobenzo[f]quinoline.

* * * * *